United States Patent [19]

Bell et al.

[11] 4,341,069
[45] Jul. 27, 1982

[54] METHOD FOR GENERATING POWER UPON DEMAND

[75] Inventors: Weldon K. Bell, Pennington; Clarence D. Chang, Princeton, both of N.J.; Reuel Shinnar, Great Neck, N.Y.

[73] Assignee: Mobil Oil Corporation, New York, N.Y.

[21] Appl. No.: 136,637

[22] Filed: Apr. 2, 1980

[51] Int. Cl.³ ............................................. F02C 3/28
[52] U.S. Cl. ................................. 60/39.02; 60/39.12; 60/39.18 B
[58] Field of Search ............. 60/39.02, 39.12, 39.18 B; 518/703, 713

[56] References Cited

U.S. PATENT DOCUMENTS

| | | |
|---|---|---|
| 3,868,817 | 3/1975 | Marion et al. |
| 3,894,102 | 7/1975 | Chang et al. ........................ 518/713 |
| 3,928,483 | 12/1975 | Chang et al. |
| 3,959,972 | 6/1975 | Rudolph et al. ..................... 518/703 |
| 3,986,349 | 10/1976 | Egan ................................. 60/39.02 |
| 4,011,275 | 3/1977 | Zahner ............................... 518/713 |
| 4,132,065 | 1/1979 | McCann. |

FOREIGN PATENT DOCUMENTS

| | | |
|---|---|---|
| 2246407 | 4/1974 | Fed. Rep. of Germany. |
| 2362944 | 7/1974 | Fed. Rep. of Germany. |
| 278353 | 9/1926 | United Kingdom. |
| WO80/00974 | 5/1980 | PCT Int'l Appl.. |

*Primary Examiner*—Louis J. Casaregola
*Attorney, Agent, or Firm*—Charles A. Huggett; Michael G. Gilman; Charles J. Speciale

[57] ABSTRACT

Fuel for satisfying low, normal and high electric power generation requirements is obtained from coal in the form of syngas and dimethyl ether fired in turbine-compressor arrangements driving electric generators, wherein the storable ether fuel is fired in turbine-generator arrangements to supplement that normally produced by firing and expanding syngas in appropriate turbine-generator arrangements. High pressure steam generated in the process is expanded in steam turbines to also generate power. Steam product of the combination operation is used in the coal gasification step to produce additional syngas.

18 Claims, 1 Drawing Figure

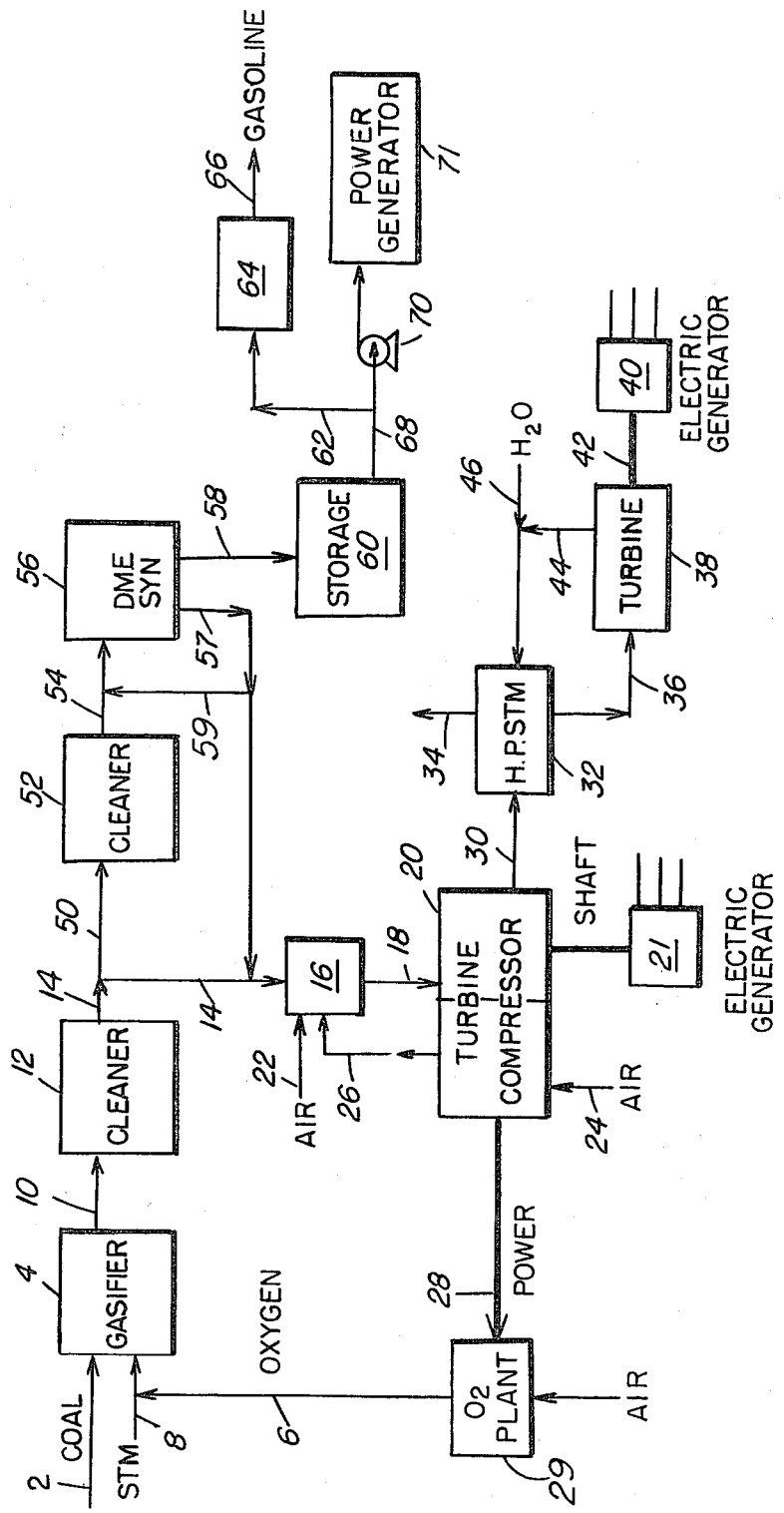

METHOD FOR GENERATING POWER UPON DEMAND

BACKGROUND OF THE INVENTION

1. Field of the Invention

This invention relates to the generation of electric power. More particularly, it is concerned with a unique method for operating an electric power plant, involving the conversion of coal to liquid and gaseous fuels which are subsequently utilized for generating electric power.

2. Discussion of the Prior Art

Solid carbonaceous materials are well known for their utility in the generation of power, particularly electrical energy. Generally, coal is combusted with air and the exothermic heat of reaction is used to produce high-pressure steam. The steam in turn is expanded through a turbine to generate mechanical or electrical energy. Similarly, natural gas and other gaseous fuels have been combusted and the heat generated used to form high-pressure steam for the generation of electrical power.

The electrical industry has developed highly efficient, large generators driven by expanding steam. However, one problem in the generation of electrical power from steam results from the greatly varying demands for electrical energy. Steam generators are not well suited for producing greatly varying amounts of steam, but rather are designed for base-load or constant-load types of operation. To provide for peak-load and reserve-load demands, the open-cycle gas turbines have generally been utilized because of their quick-startup capability and relatively low capital cost. Open-cycle turbines, however, require special fuels which are non-corrosive to the turbine blades. Generally it has been found to be uneconomical to combust coal or residual oils directly in the combination chamber of a gas turbine, because the fuel contains high amounts of ash and sulfur. Due to the incomplete combustion, such high-ash solid fuels generally produce solid particles which are abrasive and corrosive to the metal turbines. When such particles are entrained in the flue gas that is passed through the turbine, they deposit on the blades and erode the blade surfaces. When this corrosion occurs the blade is damaged, reducing the effiency of the unit, and the passages in the turbine become clogged. Further, the fine particles may deposit down-stream in heat-exchange surfaces and impair thermal efficiency. Similar problems are encountered when burning ash-producing liquid petroleum products.

Previous methods in which the fuel gas was cleaned prior to being introduced into the gas turbine were either impractical, unduly costly, or both.

The aforesaid problems of base-load and peak-load demand, combined with the special fuel requirements for gas turbines, are substantially avoided by the present invention, which integrates the production of a base-load power generation capability combined with the production of a clean, normally liquid fuel which is particularly useful for the generation of supplemental peak-load power.

Because coal and other solid carbonaceous materials often contain sulfur compounds, the combustion of coal for power production can also cause serious air pollution problems. Also, because of the very large volumes of gases produced by combustion, it is very expensive to remove the polluting sulfur compounds after combustion. These sulfur-removal problems and air-pollution problems have led to processes for the gasification of coal to produce a clean fuel gas wherein the sulfur is removed from the fuel prior to combustion. One problem, however, with such gasification processes is that only a low heat value gas is produced, and it is generally not economical to transport a low heat value gas over great distances. This has led to proposals for large on-site or "mine-mouth" gasification and power generation plants where the low heat value gas is immediately converted to electrical power for transmission. Such on-site gasification and power generation processes solve the problem of low heat gas transportation and sulfur-removal problems, but are not economical for producing greatly varying amounts of fuel as is needed for peak-load generation of power, either because it is too expensive to store gaseous products for subsequent use in gas turbines or because the capital expense of providing for greatly increasing the gas production rate and gas cleanup rate for peak-load demand is uneconomical.

The aforesaid problems are substantially avoided by the subject invention, which process provides for satisfying base-load power demand. The process integrates the production of a combustible fuel gas for meeting base-load power generation requirements with a process for producing easily storable fuels which are substantially free of sulfur and other impurities. These readily liquified fuels are suitable for storage and, when needed, for supplemental peak-load power generation.

U.S. Pat. No. 3,868,817 discloses a process for the generation of mechanical and electrical power from a purified fuel gas produced from solid carbonaceous fuels. The purified fuel gas is used to generate power using gas turbines.

Another patent, U.S. Pat. No. 3,986,349, discloses a process for generating electrical power from solid carbonaceous material in open-cycle gas turbines to meet variable power demands. The process involves the conversion of coal to a combustible synthesis gas or "syngas" by reaction with steam and oxygen. The synthesis gas is then divided into two portions, one of which is contacted with Fischer-Tropsch and hydrogenation catalysts to produce synthetic hydrocarbons ranging from methane and ethane to $C_{22}$ or higher. The normally gaseous portion of the product is separated and recombined with the second portion of the synthesis gas stream and the combined streams are combusted and utilized to operate an electricity-generating gas turbine. The normally liquid hydrocarbon product ($C_5$–$C_{22}$) is stored and utilized as fuel for a gas turbine to produce supplemental power for peak-load demand.

One of the more recent developments with regard to clean burning coal fired power plants has been the utilization of oxygen fired coal gasifiers coupled with combined-cycle power generators. In this type of plant a clean gaseous fuel obtained from the coal gasifier is burned in a gas turbine and the hot off-gases are used to generate steam. The steam is then used in a steam turbine to generate power. Heat recovered from the gasifier is used to generate additional steam, both for purposes of providing steam needed in the gasifier and as additional feed to the steam turbine.

One disadvantage to such plants has been that most coal gasifiers presently available are such that their output is neither easily nor economically varied to match the sometimes dramatic variations in power demand. The same problem results with regard to combined-cycle power plants with low efficiency if output must be reduced by more than about 20%. Many combined-cycle power plants are therefore operated in an on/off control mode.

A potential solution to this problem would be to use the syngas during times of low power demand to produce storable fuels. The oxygen-blown coal gasifiers have the advantage that they are similar to the gasifiers used for preparation of liquid fuels from coal. There are at present two processes available for use with gasifier-generated syngas for production of storable fuels: co-production of methanol and production of liquid hydrocarbons by the Fischer-Tropsch synthesis. Co-production of methanol suffers from the fact that almost all gasifiers presently contemplated for that purpose yield a synthesis gas with a low ratio of hydrogen to carbon monoxide (e.g. 0.5 to 1.0), which severely limits the amount of methanol obtainable without an additional and expensive water-gas shift. Production of hydrocarbon liquids via the Fischer-Tropsch route has the disadvantage that significant amounts of methane and ethane are produced and these are expensive to condense or otherwise separate. Also, as thermal energy is lost in the production of non-storable products from the syngas, the efficiency of the total process is greatly reduced. Our invention provides a system which overcomes these shortcomings in a way which results in an overall power generating scheme which is superior to anything previously suggested.

SUMMARY OF THE INVENTION

We have now discovered a novel method for generating power, and in particular electric power, from the gasified product of coal or other available hydrocarbonaceous materials. In the method of our invention, a substantially solid hydrocarbonaceous material such as coal, coke, oil shale residue or tar sands is converted to a gaseous mixture of hydrogen and carbon oxides by interaction with steam and oxygen. A portion of this gaseous mixture or "syngas" is burned and the hot gases are expanded in one or more power generating turbines. These turbines, which are operated in combination with compressors and/or electric power generators, provide electric power and are utilizable in periods of both high, normal and low power demand.

A second portion of the generated syngas is converted to a storable fuel product comprising dimethyl ether (DME) which, during periods of low and/or normal power demand, is passed to on-site storage facilitates. In periods of high power demand the stored fuel product is then used to either supplement the syngas feed to the power generating turbines, or else is charged separately to separate power generating turbines. The synthesis gas mixture is converted to DME by contacting the mixture with a suitable catalyst (such as Cu/Zn/Cr mixture with gamma alumina), preferably after first removing sulfur and nitrogen. Any excess DME product accumulated from the operation may conveniently be converted to gasoline boiling range hydrocarbons by contact with a special class of crystalline zeolites represented by ZSM-5 zeolite.

The combination operation of this invention, comprising coal gasification to produce syngas, expansion of burned syngas in turbines to provide electric power and the formation of DME for use as above discussed, provides an integrated operation of high efficiency for meeting the fuel requirement of high, normal and low power demand periods. More important is the fact that the coal gasification operation and the DME synthesis operation of the combination operation may be continuously carried out in a high efficiency mode. The combination operation of this invention may be varied to some extent by burning and expanding some DME produced with the syngas or separately in appropriate turbine power generating equipment. On the other hand, unreacted syngas obtained from the DME synthesis may be sufficient alone as fuel for very low electric power demand periods or it may be supplemented with fresh syngas or DME to provide fuel requirements of a low or higher power demand period.

The novel combination of processing steps provides a power generating process having considerable flexibility, particularly when employed in conjunction with a plurality of fired turbine-compressor arrangements driving electric power generators. The system offers substantial economic advantage and is responsive to the present day power variation requirements facing electric power plants.

BRIEF DESCRIPTION OF THE DRAWING

The single drawing FIGURE is a schematic flow diagram illustrating a combination process for providing low and higher power generation fuel requirements from a high efficiency coal gasification operation.

DETAILED DISCUSSION OF SPECIFIC EMBODIMENTS

A general understanding of our invention will be facilitated by consideration of the following proposed embodiment thereof, wherein reference is made to the attached drawing.

In the embodiment depicted in the drawing, coal or other hydrocarbonaceous material is charged to a coal gasifying operation 4, preferably of high efficiency, as briefly discussed hereinafter. Oxygen, or a gaseous stream containing substantial amounts of oxygen, is charged by conduit 6 to gasifier 4 and steam, or, if preferred, liquid $H_2O$, is introduced by conduit 8. Of course, the steam may be separately charged to the gasifier rather than being pre-mixed with the oxygen, the choice being dependent primarily upon the design of the gasifier and of no particular consequence to the present invention.

A coal gasification product (hereinafter referred to as syngas), preferably comprising hydrogen and carbon monoxide in a ratio compatible with the optimal efficiency of the gasification operation utilized, is recovered by conduit 10. The syngas ($H_2$/CO) in conduit 10 is thereafter at least partially cleaned in zone 12 to remove some undesired materials such as sulfur and nitrogen. A portion of the partially cleaned syngas is then passed by conduit 14 to one or more combustion zones, such as combustion zone 16, wherein the syngas is fired either in the absence or in the presence of some added fuel gas as herein discussed. Hot products of combustion then pass from combustor 16 to a power generating gas turbine-compressor prime mover 20. (For the purposes of the illustration, the hot combustor gases are shown passing to the turbine section via a conduit 18, but it should be recognized that the combustor is normally an integral part of the gas turbine.) Air may be separately supplied to the combustor by conduit 22. It is also to be recognized that there may be a plurality of such combustor-gas turbine power generating arrangements in parallel arrangement with one another and supplied with gas from conduit 14. The number of power generating turbines thus utilized will be sufficient to supply normal or less than normal power requirements as desired. In addition, air used in the system and charged by conduit 24 for compression by the gas turbine-compressor arrangement 20 may be passed in part to combustor 16 by means of conduit 26.

A preferred embodiment of the disclosed invention contemplates utilization of a portion of the power produced in the gas turbine-compressor arrangement 20 to operate an oxygen separation plant which is designed to provide the oxygen rich stream 6 for the gasifier 4. Such arrangement is shown in the drawing, wherein oxygen plant 29 represents any conventional means for obtaining an oxygen rich stream from an air feed, the power for operation of oxygen plant 29 being supplied via conduit 28 from gas turbine-compressor arrangement 20. Such an oxygen plant is, of course, optional. For the purpose of this invention, substantially any available source of oxygen or oxygen-enriched gas may be utilized to provide the oxygen required for the coal gasification operation.

Expanded hot combustion product gases are recovered from turbine-compressor 20 by conduit 30 for passage to a high pressure steam generation zone 32. Cooled combustion product gases are withdrawn from zone 32 by conduit 34 for disposal as required. High pressure steam, generated in zone 32, is passed by conduit 36 to a steam turbine 38 wherein the expanded high pressure steam generates power and drives an electric generator 40 connected to turbine 38 by shaft 42. Steam condensate may be recycled by conduit 44 to steam generation zone 32. Additional water may be brought into the system as needed via conduit 46. Turbine-compressor 20 may also be used to drive an electric generator 21 by means of a fixed shaft as shown.

A second portion of the coal gasification product from zone 12 is passed by conduit 50 to a second cleaning zone 52 wherein sulfur, nitrogen and, if preferred, $CO_2$ components are removed to a low order of magnitude, permitting catalytic conversion or restructuring of syngas to form dimethyl ether product in the presence of a sulfur sensitive catalyst. One such synthesis operation, as contemplated herein and which will be more fully discussed later, provides for the direct synthesis of dimethyl ether from syngas in the presence of a Cu/Zn/Cr methanol catalyst distributed on gamma alumina.

In the schematic flow diagram of the drawing, the cleaned syngas is shown passing from cleaning zone 52 by conduit 54 to a dimethyl ether synthesis and product separation zone 56. Unreacted syngas, separated from the DME product, is removed by conduit 57 and subsequently either charged to the combustor 16 of the gas turbine-compressor prime mover arrangement 20 or recycled by conduit 59 to the DME forming operation in zone 56.

The DME product of the synthesis operation is recovered by conduit 58 and passed to a DME storage zone 60. This DME product may be stored for subsequent use as power generator fuel during periods of peak power demand, thereby supplementing the power generated as a result of the combustion of syngas in combustion zone 16. That is, during the peak electric power load condition, the stored DME in storage zone 60 is passed by means of conduit 68 and pump 70 to one or more parallelly arranged fired turbine-compressor prime mover power generating arrangements 71. Such power generating arrangements 71 will be generally similar to that discussed above with respect to turbine-compressor arrangement 20 and to the downstream provisions following therefrom used to generate required electric power upon demand. For instance, a steam turbine power generating arrangement similar to 38 above discussed may be used in combination with zone 71 to generate additional power during times of increased power requirements by direct drive of electric generators.

Alternatively, at least a portion of the stored DME product may be converted to gasoline boiling range components. In this way the coal gasification and DME synthesis operations may be carried out at maximum efficiency and substantially constant rate, with all of the syngas not required for firing in gas turbine-compressor arrangement 20 to meet normal or low power demand being converted to DME product. Any excess DME product collected in storage zone 60, that is the amount of DME product over and above what is required to meet peak power demands, is then converted to gasoline boiling range hydrocarbons as a useful and economically very attractive by-product of the process of this invention. Such conversion is conveniently carried out by contacting the DME product with a special zeolite conversion catalyst, such as provided by U.S. Pat. No. 3,928,483 wherein methanol is dehydrated to an ether product in a first step and the formed ether product is converted with a special zeolite catalyst to gasoline boiling components. The entire content of U.S. Pat. No. 3,928,483 is incorporated herein by reference and in particular that portion thereof pertaining to the conversion of ether and the catalyst used to form gasoline boiling components therefrom. The special zeolite catalyst, known as ZSM-5 crystalline zeolite, is characterized as providing a pore opening of at least 5 Angstroms, a silica to alumina ratio of at least 12 and a constraint index within the range of 1 to 12. In this particular embodiment, a portion of the formed DME product is passed from storage zone 60 by conduit 62 to a conversion zone 64 wherein the ether is catalytically converted to gasoline boiling range product as above identified. A gasoline product, rich in olefins or aromatics or a combination thereof, depending upon reaction conditions employed, is withdrawn by conduit 66 for use as desired.

It will be apparent to those with knowledge of the combination operation that the gas turbine-compressor prime movers and the related electric and steam generators will vary in number and size, depending upon a particular capacity system. It should also be understood that more than one coal gasifier may be used in the combination operation to provide predetermined electric power requirements.

It is particularly desirable in the processing arrangement of this invention to maintain the coal gasification operation under relatively constant operating conditions and vary the turbine power output therefrom as required upon demand. The production of DME would be varied in relation to the availability of syngas not required for primary power generation. A DME reactor, unlike the coal gasifier, can be operated intermittently and generally allows for change in the rate of reactant throughput. The utilization of some of the steam generated in the process disclosed herein to provide the steam required in the coal gasification operation is also contemplated.

Heat may also be recovered from or exchanged between various conduits or systems (for example, heat could be beneficially extracted from the stream of conduit 10 or for systems 4, 56 or 64 and utilized by conduits 6, 8, 14, 22, 26, 62, 68, etc.) as befits energy conservation and fuel requirements.

Returning now to the coal gasifier, it is expected that any of the numerous commercially available processes can be utilized. It has been determined that a coal, coke or coal char gasifier using a low steam to coal ratio, such as provided by the British Gas Corporation—Lurgi slagging gasifier, has significant advantages in terms of thermal efficiency and cost which can provide a reduction of as much as 20-40% in syngas ($H_2+CO$) production costs.

An efficient gasifier is identified as one preferably having the characteristics of:
(a) using a low steam to dry, ash-free coal weight ratio of usually less than 1.0 but preferably less than about 1.5, or a low ratio of steam to syngas produced of less than 30 pounds of steam per MSCF of syngas;
(b) producing a syngas with an $H_2/CO$ ratio equal to or less than 1; and
(c) a low temperature exit gas of less than 1094° C. (2000° F.).

Examples of gasifiers satisfying the above characteristics include slagging type gasifiers, such as the previously mentioned British Gas Corporation—Lurgi slagger or the Second-Grate slagging gasifier, or a fluidized bed gasifier such as the U-gas or the Westinghouse gasifiers.

Some gasifiers, such as the Texaco gasifier or the Shell-Koppers gasifier, have a high exit temperature which is detrimental for most syngas conversion processes. However, since combined cycle power plants (as discussed herein) have the capability of recovering and using at least some of the heat in the combined cycle, such gasifiers are much less detrimental when employed in the present invention and, in some situations, are even preferable. This is particularly so since such gasifiers are known to provide a syngas product having a low $H_2/CO$ ratio.

Gasifiers which provide a syngas product having a high $H_2/CO$ ratio use large amounts of excess steam in their operation. Since it is difficult to recover the heat of condensation efficiently, such gasifiers, as for example the Lurgi Dry Ash gasifier, are less efficient (but nonetheless utilizable) in combined cycle power plants. Also, as hydrogen has a 20% lower heating ratio per mole relative to carbon monoxide, utilization of excess steam to bring about a water-gas shift in the gasifier is detrimental to the overall thermal efficiency of the plant.

The gasifiers contemplated for use in the combination process of this invention may be operated over a wide range of pressures, it being preferred to use a pressure within the range of 300 to 1500 psig, primarily for economic reasons.

Most modern gasifiers, such as those discussed above, when operated in the efficient mode for which they were designed, produce a syngas product stream having a $H_2/CO$ ratio approximately equal to 1. More usually, for the highest efficiency gasifiers, the ratio is less than one and within the range of about 0.4 to about 0.8. Such low ratio $H_2/CO$ syngas cannot be utilized without additional water-gas shift in the conventional Fischer-Tropsch (to produce liquid hydrocarbon fuels) or methanol synthesis processes, both of which require $H_2/CO$ gas ratios equal to or greater than 2. Thus, any external water-gas shift operation to increase a low syngas ratio of 1 or less up to a required 2 or more would substantially cancel any gains in efficiency achieved by the most advanced gasifiers. Also, the production of Fischer-Tropsch liquids has the disadvantage that significant amounts of methane and ethane, which are expensive to condense or separate, are produced. We have found that the direct synthesis of dimethyl ether from syngas avoids these problems and, at the same time, provides an easily stored product which may be readily burned as supplemental fuel for the turbines or conveniently converted to gasoline boiling range hydrocarbons.

Prior to the present disclosure, two patents dealing with synthesizing DME directly were known. These include British Pat. No. 278,353 (1926) to F. R. Bechowsky and German Offenlegungsschrift No. 2,362,944 (1974) issued to G. Pagani. The British patent discloses a process for producing dimethyl ether by contacting synthesis gas ($H_2/CO$) with a hydrogenating catalyst and a dehydrating catalyst at elevated temperatures and pressure. In this patent, DME synthesis was obtained in the absence of the known shift reaction. In the German patent, the catalyst comprised a methanol synthesis component and a dehydrating component. In one example, a gas with $H_2/CO=0.86$ was contacted with a catalyst comprising Cu/Zn/Cr in an atomic ratio of 82/16/4, supported on alumina, at 900° C. and 1422 psia. The conversion of the syngas was 77%. The exit gas contained 24.2% DME, 0.91% MeOH, 27.3% $CO_2$, 0.41% $H_2O$, 0.54% $CH_4$, with the balance being $H_2$, CO and $N_2$.

The preferred synthetic route for the conversion of syngas to dimethyl ether, alone or in admixture with minor amounts of methanol in the feed or separately added, is carried out in the presence of an oxygen regenerable catalyst. A particularly preferred catalyst composition and an acceptable and effective oxidative regeneration technique therefor are disclosed in U.S. application Ser. No. 72,742 (filed Sept. 4, 1979), which is incorporated herein by reference. The catalyst is maintained at a desired level of activity and selectivity in this operation sufficient to sustain conversion of the syngas feed to DME over an extended operating period.

The preferred method of conversion of syngas to DME relies upon using metal components of a methanol synthesis catalyst in a particular relationship and in combination with a method of preparation fulfilling hereindescribed restricting parameters of hydrogenating components in combination with an acidic dehydrating component. More particularly, the preferred DME synthesis catalysts used in the present invention rely upon the technique of coprecipitation of the metal components Cu, Zn, Cr or Al of a methanol synthesis catalyst used in admixture with an acidic dehydrating component. This combination provides an oxygen regenerable catalyst, particularly when the atomic ratio of Cu, Zn and Cr is varied within relatively narrow limits herein specifically identified. More particularly, the coprecipitated components of Cu, Zn and Cr are used in a ratio with respect to one another such that the ratio of Cr/(Cu+Zn) is in the range of 0.1 to 1.0 and more preferably within the range of 0.25 to 0.75. A ratio of 0.5 is especially preferred. On the other hand, the ratio of Cu/Zn is preferably within the range of 0.5 to 3.0.

The acidic dehydrating component or matrix supporting material of the catalyst composition may be any material suitable for the purpose and preferably selected from the group consisting of gamma alumina, silica-alumina, ZSM-5 crystalline zeolites of high $SiO_2$ content, phosphates, titanium oxide in combination with silicon oxide, rare earths and clays. Of these compositions, it is preferred to use gamma alumina in an amount within the range of 20 to 85 weight percent of the catalyst composition, with from about 25 to about 50 weight percent being particularly preferred.

The dimethyl ether synthesis techniques of this invention are of particular and novel interest upon noting that $H_2/CO$ ratio gases of either less than 1 or greater than 1 can be employed. Thus the ratio of $H_2/CO$ may be within the range of 0.5 to 3. However, it is preferred to employ gas ratios equal to or less than 1, since such gas ratios are much more economically produced by modern high efficiency gasifiers, as briefly discussed above, and such a source of syngas can result in from 30% to 40% overall reduction in processing costs. In this syngas conversion operating environment, it has been determined that the hydrogen deficiency of the low ratio syngas in the range of 0.4 to 0.7 can be modified by water-gas shift to an $H_2/CO$ ratio gas of 1 or more. That is, by injecting or otherwise providing steam ($H_2O$) in contact with the special catalyst composition and in admixture with the low ratio syngas charged to the ether synthesis zone, the desired water-gas shift can be achieved. This added steam ($H_2O$) is subject to water-gas shift reaction during DME synthesis by the catalyst to effectively provide an $H_2/CO$ ratio gas of 1 or more as desired in the catalyst reaction zone. This water addition will vary with the syngas $H_2/CO$ ratio charged, but such addition effectively eliminates the need for expensive and separate external water-gas shift equipment to modify a low ratio syngas. It also avoids the penalty of excess steam required in a separate shift reactor. This method of operation further contributes to the overall economics of the improved power providing processing combination.

Thus the water-gas shift characteristics of the catalyst and oxidative regeneration capability thereof to sustain catalyst activity also contribute measurably to the economic improvement and synergistic relationship of the combination operation.

As mentioned above, dimethyl ether synthesis offers decided advantages over Fischer-Tropsch and methanol synthesis operations, since DME synthesis lends itself particularly to utilizing a relatively low ratio syngas, e.g. $H_2/CO=1$. This particular syngas conversion operation can be used with considerable advantage in combination with any high efficiency coal gasification operation producing either high or a low ratio syngas. The addition of water (steam) with low ratio syngas to promote the shift reaction is used to considerable advantage with a low ratio syngas feed when passed in contact with the DME synthesis catalysts of this invention. In this novel synthesis and combination operation, the catalysts' water-gas shift capability and process generated steam are utilized to advantage. The efficient utilization of generated synthesis gas ($H_2/CO$) by coal gasification is a primary objective of the combination process of this invention. Of particular interest in this power distribution operation is the application of dimethyl ether synthesis at pressures near those anticipated and desired for the most modern coal gasifying systems. The companion application above identified relates particularly to some high pressure DME synthesis operations. The present application identifies by Table 1 below the product distribution obtained with two different catalysts under different pressure conditions and feed compositions.

Methanol and DME are those liquefiable fuels which retain a maximum of heat value from syngas conversion as compared with other fuels. However, when relying upon a gasifier producing a low ratio of syngas, $H_2/CO=1$ or less, the formation of methanol is not an ideal choice. DME offers thermodynamic incentives over methanol in terms of the equilibrium conversion limits for the methanol or DME reaction sequence for the reasons discussed above.

The conversion of the syngas feed to an ether product, using the catalyst compositions herein defined, is accomplished at a temperature within the range of 260°–427° C. (500° to 800° F.) and preferably less than 400° C. (750° F.), at a pressure within the range of 300 to 2000 psig, and at a GHSV (gas hourly space velocity) within the range of 100 to 10,000, preferably 1000–4500.

In the power generating operation of the invention and the distribution of fuel required in the operation, interest necessarily centers on the balance of operating pressures required in the process. A compatible relationship of syngas conversion to DME at pressures near that desired for modern high efficiency coal gasifiers is therefore of particular interest. The various pressure operations of Table 1 relate to low, medium and high pressure operations with two different identified catalysts.

TABLE 1

DIMETHYL ETHER SYNTHESIS PRODUCT 18 HOURS AFTER CATALYST REGENERATION

|  | Catalyst 1 | | Catalyst 2 | |
|---|---|---|---|---|
| FEED: | | | | |
| $H_2/CO$ | 1.0 | 1.0 | 0.67 | 0.67 |
| $H_2O/CO$ | 0 | 0 | 0.25 | 0 |
| REACTION CONDITIONS: | | | | |
| Days Opr. | 69 | 74 | 30 | 71 |
| Temperature, °C. | 316 | 316 | 316 | 316 |
| Pressure, psig | 1460 | 500 | 780 | 500 |
| GHSV | 2000 | 990 | 1200 | 1047 |
| WHSV | 1.28 | 0.63 | 0.98 | 0.86 |
| REACTOR PRODUCT DISTRIBUTION (WT. %): | | | | |
| $H_2$ | 1.4 | 3.0 | 1.9 | 2.0 |
| CO | 26.4 | 56.2 | 31.3 | 65.8 |
| $CO_2$ | 31.5 | 22.6 | 45.5 | 17.2 |
| $H_2O$ | 0.3 | <0.1 | 0.6 | 0.4 |
| DME | 38.7 | 16.6 | 19.3 | 13.7 |
| MeOH | 1.5 | 0.3 | 1.3 | 0.6 |
| $CH_4$ | 0.2 | 0.7 | 0.1 | 0.2 |
| $C_2^+$ | <0.1 | 0.4 | <0.1 | 0.1 |
| CONVERSIONS (MOLE %): | | | | |
| $H_2$ | 79.3 | 55.2 | 52.2 | 55.9 |
| CO | 71.7 | 39.8 | 62.3 | 31.1 |
| Total | 75.5 | 47.5 | 58.3 | 41.0 |

Catalysts 1 and 2 of Table 1 were prepared in two parts. First, a methanol metal component catalyst was prepared by coprecipitation of three different metal components from an aqueous stirred solution of their nitrates by the addition of excess hot (85°–90° C.) sodium carbonate solution. The resulting precipitate was washed, dried and calcined at about 260° C. (500° F.).

These methanol components were then ground to powders and each was combined with an equal part by weight of a gamma alumina powder.

Catalyst 1 had methanol metal components prepared from equal atom amounts of copper, zinc, and chromium. Catalyst 2 had methanol metal components prepared from equal atom amounts of copper, zinc, and aluminum.

Both catalysts were initially activated by contacting at 1 atm. and 204° C. (400° F.) with a hydrogen/inert purge gas stream mixture whose hydrogen composition was slowly increased to 2 volume percent and then to 8.5 volume percent. The catalysts were then operated at synthesis conditions for extended periods with periodic oxidative catalyst regeneration as required. These oxidative regenerations were carried out by purging the reactor with an inert purge gas such as nitrogen; passing over the catalyst a pulse of oxygen of 100 liters STP/liter catalyst at atmospheric pressure and at a temperature in the range of 288°–343° C. (550° to 650° F.) and a space velocity sufficiently slow to prevent thermal damage to the catalyst; and then gradually displacing the inert purge gas stream at reaction conditions with syngas charge.

EXAMPLES WITH CATALYST 1

Catalyst 1 was contacted with synthesis gas providing an $H_2/CO$ ratio of 1/1 at 316° C. (600° F.) and 100 atm total pressure and operated at gas hourly space velocities (GHSV) in the range of from 1000 to 4300 $hr^{-1}$ for 76 days with oxidative regenerations as above described on 3 day or daily regeneration schedules [between 55 and 65 days at on-stream lower reaction temperatures of 293° C. (560° F.) and 271° C. (520° F.)]. The results of material balances obtained about 18 hours after catalyst regenerations are presented in Table 1 for 69 and 74 days on stream. The results obtained are typical of the behavior of this catalyst under stable operating conditions at 100 atm and 35 atm following catalyst regeneration.

EXAMPLES WITH CATALYST 2

Catalyst 2 was contacted at 316° C. (600° F.) with synthesis gas providing an $H_2/CO$ ratio of 0.67 for 8 days at 52 atm and GHSV=1050, and then for 62 days at 54 atm with a water cofeed of 0.25 mole $H_2O$/mole CO at GHSV=1200 and periodic catalyst oxidative regenerations (about every 10 days), and then at 35 atm and GHSV=1050 without water cofeed. The results of the material balances obtained at 30 and 71 days on stream (each taken 18 hours after catalyst regeneration) are also presented in Table 1 as typical of regenerated catalyst behavior at 54 and 35 atm.

It will be observed from the data of Table 1 that significant yields of DME are produced in the absence of producing considerable methanol and methane at the different pressure conditions using $H_2/CO$ ratio gas of 1 and less. These operating conditions and variations thereon can be adapted to modern coal gasifying systems with a minimum of effort to achieve the results desired in the combination operation of the invention.

A significant advantage is obtained by producing DME in that low ratio syngas can be used as feed, the produced DME is storable, and the produced DME can be used as fuel for electric power generation or as a feed to catalyst operation converting the DME to gasoline hydrocarbons, or both. Furthermore, steam generated in the combination operation is available for use in the coal gasifying operation. This synergistic relationship in operating economy and efficiency provides a significant contribution in an energy deficient environment.

The ether product of the synthesis operation may be separated from unreacted syngas, for instance by cooling and/or absorption in alcohol, and then passed to storage for subsequent use as herein provided. The separated unreacted syngas obtained from DME synthesis, with or without methane, is passed to a fired turbine of a turbine-compressor prime mover for power recovery. In some design arrangements, the unreacted syngas for converted to an ether product may be sufficient alone as fuel for a low power demand period requirement or it may be used in combination with syngas directly obtained from a coal gasification operation following the removal of sulfur and nitrogen as required. Thus the combination operations contemplated by the present invention vary in several different respects, but permit using all or part of a coal gasification product comprising hydrogen, carbon monoxide and a synthesized DME product to provide both low and high power requirements upon demand.

In an alternate embodiment to that previously discussed with reference to the drawing, it is contemplated that it may be desirable in some applications of the invention to pass substantially all of the syngas output of the gasifier 4 to the DME synthesis operation 56. In such case, the cleaner 12 and conduit 14 may be eliminated. The novel process remains essentially the same, except now the unreacted syngas in conduit 57 is substituted for the portion of the syngas stream previously routed via conduit 14 to combustor 16. This embodiment is expected to be particularly advantageous in power plant applications wherein the fuel requirements for the low power demand periods (e.g. after 9:00 PM and on weekends) can be fully satisfied by consumption of about 40% of the syngas generated by the gasifier. Since the preferred method of DME synthesis will generally provide for approximately 50–60% conversion of the syngas, the separated unreacted syngas, instead of being recycled via recycle loop 59, will be substantially the amount needed to supply the fuel required to meet such periods of low power demands. The synthesized DME will be accumulated in storage 60 for subsequent use during periods of normal and high power demands, as discussed previously, with the excess DME, if any, being converted to gasoline boiling range product.

A further advantage in producing dimethyl ether directly from syngas is that it has been found that this compound may be readily converted to gasoline boiling range hydrocarbons when using a special class of crystalline zeolites represented by ZSM-5 zeolite, such as discussed in the aforementioned U.S. Pat. No. 3,928,483. In this patent, methanol is dehydrated to form the ether product thereof which is then converted to higher boiling hydrocarbons by contact with the special class of crystalline zeolites.

The novel combination of processing steps comprising this invention solves a long felt electric power generating problem with considerable flexibility and economic advantage and is responsive to the present day power variation requirements. The combination operation of the invention provides several significant advantages:

1. It allows for a higher recovery of storable fuel than does coproduction with methanol alone, especially with the more modern thermally efficient gasifiers which provide an $H_2/CO$ ratio considerably below 2 and more usually less than 1. If the low ratio syngas is used as is, methanol conversion is limited to 25–30% of the available energy. If, on the other hand, the low ratio syngas is shifted externally, there is a severe energy penalty for the steam required for such shift to a higher ratio syngas. For either syngas product, conversions thereof of up to 50% are possible without water-gas shift. However, introduction of small amounts of steam directly into the syngas conversion reactor will allow for single pass conversion of the low ratio syngas charge of up to 80% or higher.

2. The higher syngas conversion leads to higher thermal efficiency. For any chemical conversion of the syngas, a cleaner gas is required as compared to direct combustion. The energy requirement and cost of this clean-up are essentially equal for either of the methanol or the combined methanol-dimethyl ether conversion operation and this results in cheaper cost and much higher thermal efficiency in the combination operation.

3 The combination operation of the invention is better than Fischer-Tropsch synthesis, since no substantial amount of non-condensable gaseous by-products are produced. Production of $CH_4$ and ethane by the Fischer-Tropsch process reduces the overall process thermal efficiency, as these gases cannot be economically separated for storage and have a lower heat value content than does the syngas used in their production. However, conversion of the syngas to DME produces little, if any, methane and ethane. Consequently their separation is not a problem.

The system also has some unexpected synergistic advantages for the production of ether. If a methanol-dimethyl ether mixture is the sole required product, dimethyl ether has to be separated from coproduct $CO_2$. Furthermore, the $CO_2$ thus separated must be freed from traces of ether before release to the environment. These separations are expensive and are unnecesary in the combination process of this invention, since the total product is burned as required an all $CO_2$ passes with the ether product through the combustor associated with the turbine. Any $CO_2$ dissolved in the ether-methanol mixture does not affect the storability of the fuel or use of the ether fuel in a turbine power recovery expander.

Having thus generally described the method and combination process of the present invention and discussed specific examples in support thereof, it is to be understood that no undue restrictions are to be imposed by reason of the specific illustration except as defined by the following claims.

We claim:

1. A method for generating power from coal which comprises:
   (A) gasifying coal in the presence of steam and oxygen to generate a syngas comprising hydrogen and carbon oxides;
   (B) passing a first portion of the generated syngas to a fired turbine-compressor prime mover driving an electric generator and expanding fired syngas in the turbine thereof, and passing compressed air from said turbine-compressor prime mover to said fired turbine;
   (C) removing sulfur and nitrogen from a second portion of said generated syngas and passing said second portion in contact with a catalyst and under conditions to synthesize a dimethyl ether product, passing unreacted syngas separated from said dimethyl ether product to one of said dimethyl ether synthesis reaction step or to said fired turbine; and
   (D) passing synthesized dimethyl ether to a storage zone and passing dimethyl ether from said storage zone to a fired turbine-compressor prime mover electric power generator.

2. The method of claim 1 wherein hot gases are recovered from a fired turbine, said recovered hot gases are used to generate high pressure steam, said high pressure steam is expanded in a steam turbine driving an electric generator and there are a plurality of said fired and steam turbines employed in combination with one another to generate variable electric power requirements.

3. The method of claim 1 wherein the synthesized dimethyl ether is employed in a fired turbine as auxiliary fuel during power generating requirements above that provided by said fired syngas.

4. The method of claim 1 wherein there are a plurality of syngas and dimethyl ether fired turbines in parallel arrangement with one another to provide high power requirements.

5. The method of claim 1 wherein there is more than one high efficiency coal gasification operation providing syngas for use in the combination operation.

6. The method of claim 1 wherein a portion of the synthesized dimethyl ether is converted to gasoline boiling hydrocarbons.

7. The method of claim 1 wherein the coal gasification operation and the dimethyl ether synthesis operation are conducted under high efficiency operating conditions and fuel for the fired turbine during high power requirements is provided by the ether product.

8. The method of claim 1 wherein said synthesis of said dimethyl ether product is carried out intermittently, during periods of low power demand.

9. A method for producing fuels for use in generating electric power during low, normal, and high power requirements, which method comprises:
   (A) generating syngas comprising hydrogen and carbon monoxide in a coal gasification operation;
   (B) converting a portion of the generated syngas to a storable fuel product comprising dimethyl ether and subsequently passing the dimethyl ether to storage;
   (C) employing syngas from said coal gasification and said stored dimethyl ether as fuel in a plurality of fired turbine-compressor arrangements driving electric power generators; and
   (D) providing the low, normal and high electric power requirements by varying the amount of dimethyl ether and syngas fired in said plurality of fired turbine-compressor arrangements.

10. The method of claim 9 wherein one or more high efficiency coal gasifiers are employed to generate syngas, the syngas is cleaned partially for sulfur removal before combustion in a fired turbine, a more complete sulfur removal is effected from the portion of said syngas which is converted to dimethyl ether with a sulfur sensitive catalyst, hot gases recovered from said fired turbine are used to generate steam and a plurality of steam turbines are employed in the combination operation to drive electric generators.

11. The method of claim 9 wherein unreacted syngas is recovered from the dimethyl ether forming step and said unreacted syngas is passed to a fluid turbine-compressor arrangement generating electric power.

12. A method for generating power from coal which comprises:
   (A) gasifying coal in the presence of steam and oxygen to generate a syngas comprising hydrogen and carbon oxides;
   (B) removing sulfur and nitrogen from said generated syngas and passing said syngas in contact with a catalyst and under conditions suitable to synthesize a dimethyl ether product;

(C) passing unreacted syngas separated from said dimethyl ether product to a fired turbine-compressor prime mover driving an electric generator and expanding fired syngas in the turbine thereof; and (D) passing synthesized dimethyl ether to a storage zone and passing dimethyl ether from said storage zone to a fired turbine-compressor prime mover electric power generator.

13. The method of claim 12 wherein hot gases are recovered from a fired turbine, said recovered hot gases are used to generate high pressure steam, said high pressure steam is expanded in a steam turbine driving an electric generator and there are a plurality of said fired and steam turbines employed in combination with one another to generate variable electric power requirements.

14. The method of claim 12 wherein the synthesized dimethyl ether is employed in a fired turbine as auxiliary fuel during power generating requirements above that provided by said fired syngas.

15. The method of claim 12 wherein there are a plurality of syngas and dimethyl ether fired turbines in parallel arrangement with one another to provide high power requirements.

16. The method of claim 12 wherein there is more than one high efficiency coal gasification operation providing syngas for use in the combination operation.

17. The method of claim 12 wherein a portion of the synthesized dimethyl ether is converted to gasoline boiling hydrocarbons.

18. The method of claim 12 wherein the coal gasification operation and the dimethyl ether synthesis operation are conducted under high efficiency operating conditions and fuel for the fired turbine during high power requirements is provided by the ether product.

* * * * *